United States Patent
Arabian et al.

(10) Patent No.: US 7,159,474 B2
(45) Date of Patent: Jan. 9, 2007

(54) MODULAR SAMPLING DEVICE

(75) Inventors: Adam K. Arabian, Louisville, KY (US); Charles K. Kerechanin, II, Burtonsville, MD (US); Stuart D. Harshbarger, Woodbine, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/941,573

(22) Filed: Sep. 15, 2004

(65) Prior Publication Data

US 2005/0081653 A1    Apr. 21, 2005

Related U.S. Application Data

(60) Provisional application No. 60/504,115, filed on Sep. 18, 2003.

(51) Int. Cl.
*G01N 1/00* (2006.01)
(52) U.S. Cl. .................................. 73/863.23
(58) Field of Classification Search ............ 73/863.21, 73/863.22, 863.23, 863.24, 863.25; 15/347–353
See application file for complete search history.

(56) References Cited

U.S. PATENT DOCUMENTS

| | | | |
|---|---|---|---|
| 3,748,905 A | | 7/1973 | Fletcher et al. |
| 4,246,788 A | * | 1/1981 | Olin et al. ............... 73/863.03 |
| 4,961,916 A | | 10/1990 | Lesage et al. |
| 5,005,430 A | | 4/1991 | Kibler et al. |
| 5,333,511 A | | 8/1994 | Boyum et al. |
| 5,500,369 A | | 3/1996 | Kiplinger |
| 5,693,895 A | | 12/1997 | Baxter |
| 5,939,647 A | | 8/1999 | Chinn et al. |
| 2002/0083780 A1 | * | 7/2002 | Lutz et al. ............... 73/863.01 |
| 2003/0015098 A1 | | 1/2003 | Robertson et al. |
| 2003/0226232 A1 | * | 12/2003 | Hayashi et al. ............... 15/353 |
| 2004/0043443 A1 | | 3/2004 | Lejeune |

* cited by examiner

*Primary Examiner*—Daniel S. Larkin
(74) *Attorney, Agent, or Firm*—Benjamin Y. Roca

(57) ABSTRACT

A sampling device is disclosed. The sampling device is portable and capable of taking two samples in parallel. The sampling device can include two filter locations that are subjected to similar environmental conditions. The sampling device design facilitates easy assembly and disassembly, and can be designed so that a single filter holder design can be used in both filter locations.

2 Claims, 5 Drawing Sheets

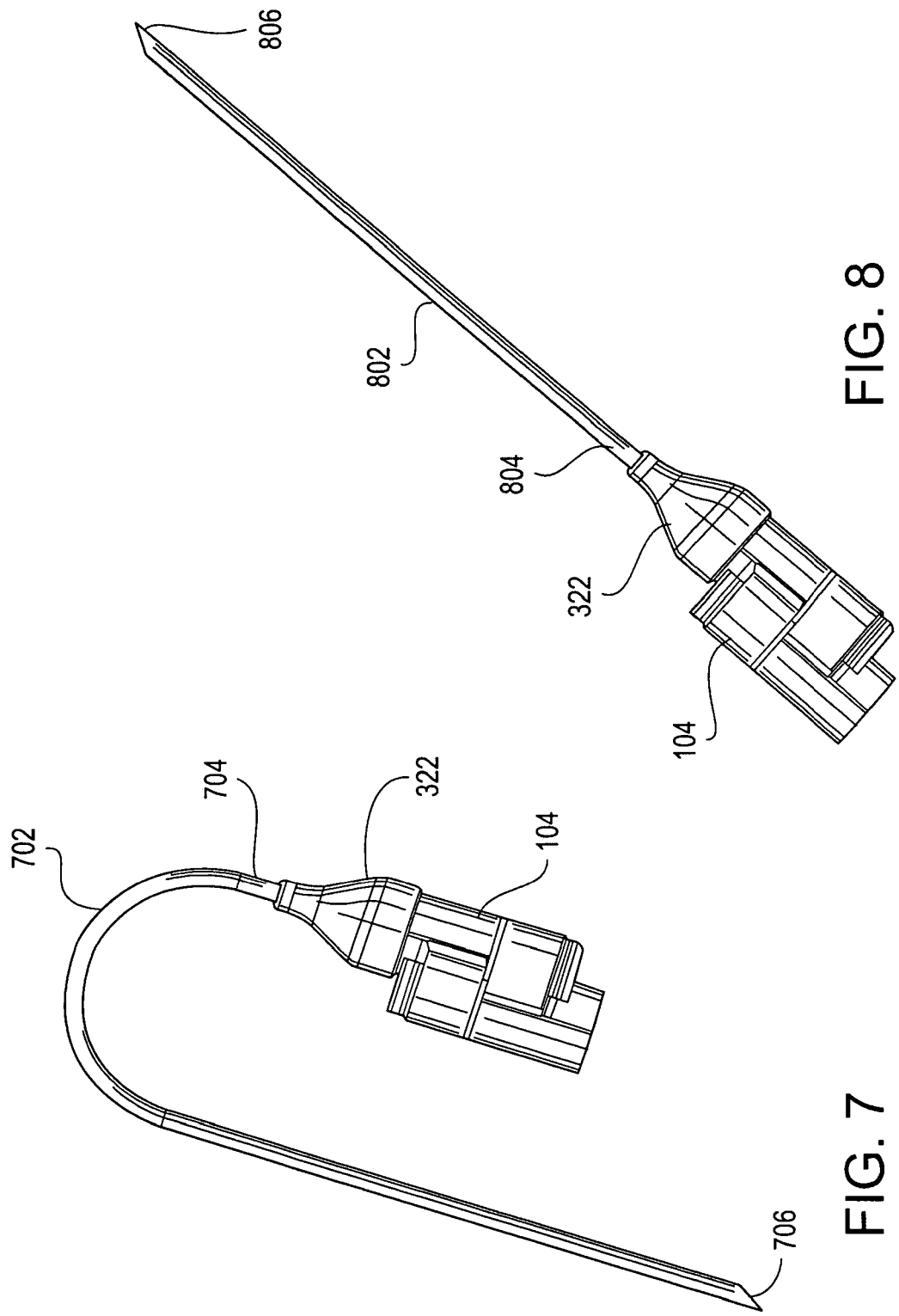

MODULAR SAMPLING DEVICE

CROSS REFERENCE TO RELATED APPLICATIONS

This application claims the benefit of U.S. Provisional Patent Application No. 60/504,115, filed on Sep. 18, 2003. This Provisional Patent Application is hereby incorporated by reference in their entirety.

STATEMENT OF GOVERNMENT INTEREST

This invention was made with Government support under Contract Number N00024-98-D-8124 awarded by Naval Sea Systems Command. The Government may have certain rights in this invention.

BACKGROUND OF THE INVENTION

1. Field of the Invention

This invention relates to a sampling device, and more particularly, to a modular sampling device.

2. Related Art

When there is a potential threat of exposure to nuclear, biological or chemical (NBC) materials, precautions are often taken. These precautions can include early detection and warning of the presence of NBC materials. In some cases, it is necessary to take samples in areas where the detection of NBC materials is not routinely done. In these cases, it is necessary to use portable sampling equipment.

In some cases, it is necessary to take two samples, one sample to immediately test for the presence of NBC materials, and a second sample to either archive or subject to a different kind of test. It is also helpful if the sampling media, for example, filters, are easy to install and remove. While various sampling devices have been proposed, the related art fails to teach or disclose such a device.

Boyum et al. (U.S. Pat. No. 5,333,511) discloses a device that draws in air at preset timed intervals through a valve mechanism. The Boyum device does not take two samples in parallel and the sampling media is not easy to install and remove. It also appears to be directed to sampling solely gases, and cannot be used for aerosolizable particulates.

Chinn et al. (U.S. Pat. No. 5,939,647) discloses a surface particle sampling head with a rotating probe. Chinn discloses a device that is set on a surface to create a seal. After the seal is created, air is blown on the surface and particles are funneled to a particle analysis device. The Chinn reference lacks a means for sampling because Chinn performs internal testing with a particle counter. Thus, the Chinn device does not provide a filter, much less dual filters. Chinn also uses compressed gas as an agitator. Chinn also discloses the use of Teflon as one of the main materials. This is disadvantageous, because Teflon tends to hold charge and attract particles, thus preventing effective sampling. The Chinn device does not collect sampling matter onto a filter.

Robinson et al. (U.S. patent application number 2003/00150985) discloses a cassette for use with vortex separation and sampling of particles. Systems that use vertex separation are not adaptable for portable devices because they generally require a vertical orientation to work efficiently. Robinson fails to teach the use of dual filtration.

Lejeune (U.S. patent application number 2004/0043443) teaches two sampling inlets and two filters. However, the Lejeune device does not include a common inlet and is not portable. Because Lejeune draws from two separate inlets, the two filters may not receive the same representative sample. The Lejeune device is also intended to be permanently installed and is not portable.

While the related art generally teaches sampling devices, none of the references teach a portable system capable of taking two similar representative samples where the sampling media is easy to install and remove.

SUMMARY OF THE INVENTION

In one aspect, the invention provides a sampling device configured to cooperate with an inlet device at an inlet and an air pump comprising: a central housing including an upstream portion and a downstream portion; the upstream portion including provisions to receive a first filter holder, the first filter holder containing a first filter; the downstream portion including provisions to receive a second filter holder, the second filter holder containing a second filter; wherein sampling matter is drawn into the inlet and divided into a first stream that interacts with the first filter and a second stream that interacts with the second filter; and wherein the first filter holder and the second filter holder are substantially similar in shape and size.

In another aspect, the invention provides a first filter holder that is disposed upstream of the second filter holder.

In another aspect, the second stream enters a first flow passage of the central housing after entering the inlet.

In another aspect, the first filter holder includes a flow passage adjacent to the first flow passage of the central housing.

In another aspect, the flow passage of the first filter holder and the first flow passage of the central housing form the inlet.

In another aspect, the flow passage of the first filter holder is generally semi-circular and the first flow passage of the central housing is generally semi-circular and both the flow passage of the first filter holder and the first flow passage of the central housing form a generally circular inlet.

In another aspect, the first filter holder is disposed on an upstream portion of the central housing and the second filter holder is disposed on a downstream portion of the central housing.

In another aspect, the flow passage of the first filter holder and the first flow passage of the central housing form the inlet.

In another aspect, the invention provides a sampling device comprising: a central housing including an upstream portion and a downstream portion; a first filter associated with the upstream portion; a second filter associated with the downstream portion; wherein sampling matter is drawn into the inlet and divided into a first stream that interacts with the first filter and a second stream that interacts with the second filter; and wherein the second filter is axially spaced from the first filter.

In another aspect, the second stream enters a flow passage prior to interacting with the second filter.

In another aspect, first stream enters a flow passage after interacting with the first filter.

In another aspect, a first filter holder includes a disk portion containing the first filter and a flow passage portion.

In another aspect, a second filter holder holds the second filter and is substantially similar to the first filter holder.

In another aspect, the invention includes a scraper attachment.

In another aspect, the invention provides a method for assembling a sampling device comprising the steps of: installing a first filter into a first filter holder; installing a second filter into a second filter holder; associating the first filter holder with a central housing in an upstream end; and associating the second filter holder with the central housing on a downstream end.

In another aspect, a 47 mm round filter is installed into the first filter holder.

In another aspect, the first filter holder is substantially similar to the second filter holder.

In another aspect, a seal is provided between the first filter holder and the central housing.

In another aspect, the filter is installed into the filter holder prior to the step of associating the filter holder to the central housing.

In another aspect, a portion of the installed first filter holder and a portion of the central housing form a generally circular inlet port after assembly.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 7 is a schematic diagram of a preferred embodiment of a sampling device with a curved wand.

FIG. 8 is a schematic diagram of a preferred embodiment of a sampling device with a straight wand.

DETAILED DESCRIPTION OF THE PREFERRED EMBODIMENT(S)

Figure 1:
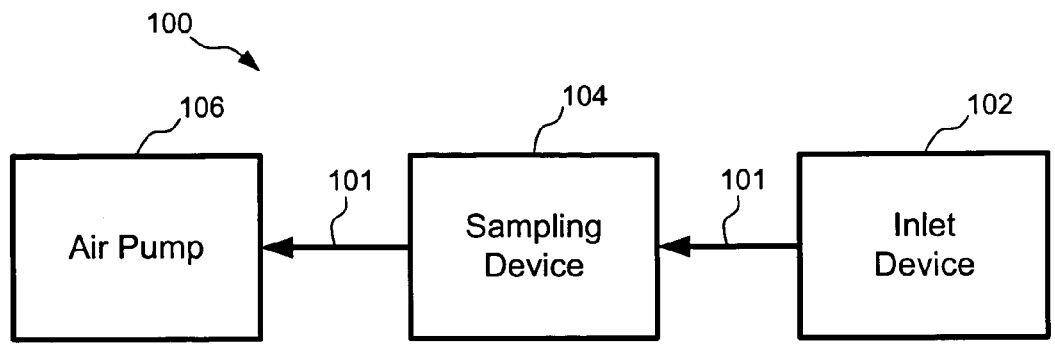
FIG. 1 is a schematic diagram of a preferred embodiment of a sampling system.

FIG. 1 is a schematic diagram of a preferred embodiment of a sampling system 100, which has a flow direction 101 and includes at least three devices. Inlet device 102 serves as a first stage and is preferably upstream of sampling device 104 and air pump 106.

In the embodiment shown in FIG. 1, inlet device 102 can include an inlet that opens to an environment where a sample is to be taken. In some embodiments, disclosed below, inlet device can include inlets of various designs, nozzles, tubes, scrapers and/or combinations of these types of devices.

Sampling device 104 comprises a second stage downstream of inlet device 102 but upstream of air pump 106. Sampling device 104 collects various samples. In a preferred embodiment, second stage 104 includes one or more filters that are designed to collect and retain sampled matter. Air pump 106 serves as a third stage and is preferably disposed downstream of sampling device 104. Different devices, including fans, blowers, vacuum pumps and other fluid motors can serve as air pump 106. Preferably, air pump 106 is capable of providing a desired flow rate or pressure drop across sampling device 104 for a selected sampling application.

Figure 2:
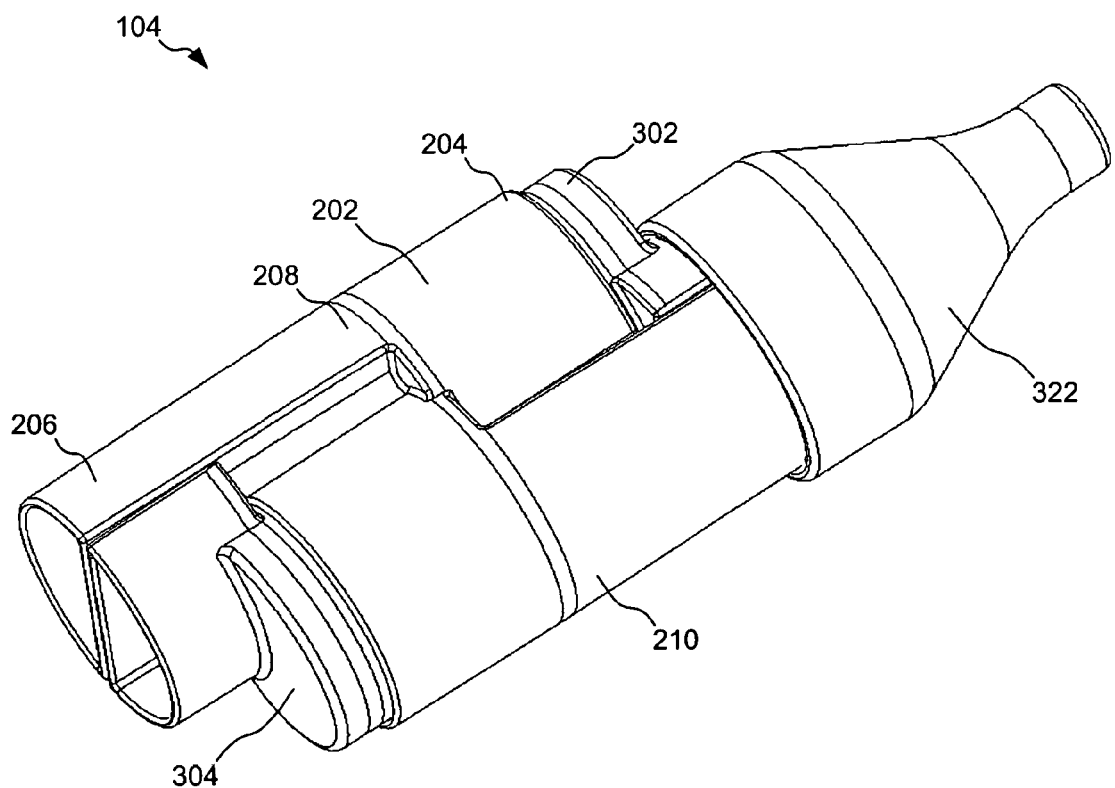
FIG. 2 is a schematic diagram of a preferred embodiment of a sampling device.
Figure 3:
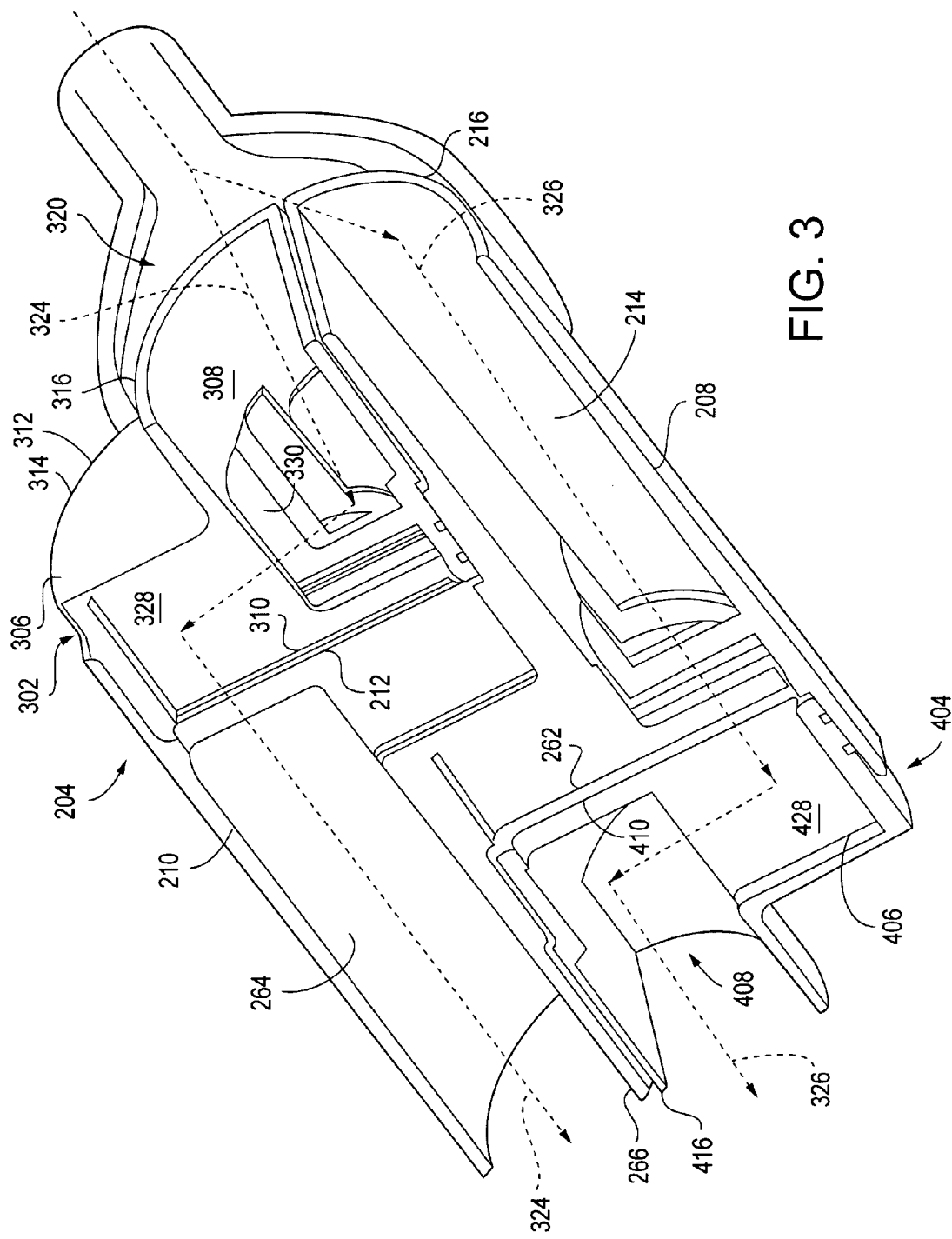
FIG. 3 is a schematic cross-sectional view of a preferred embodiment of a sampling device.
Figure 4:
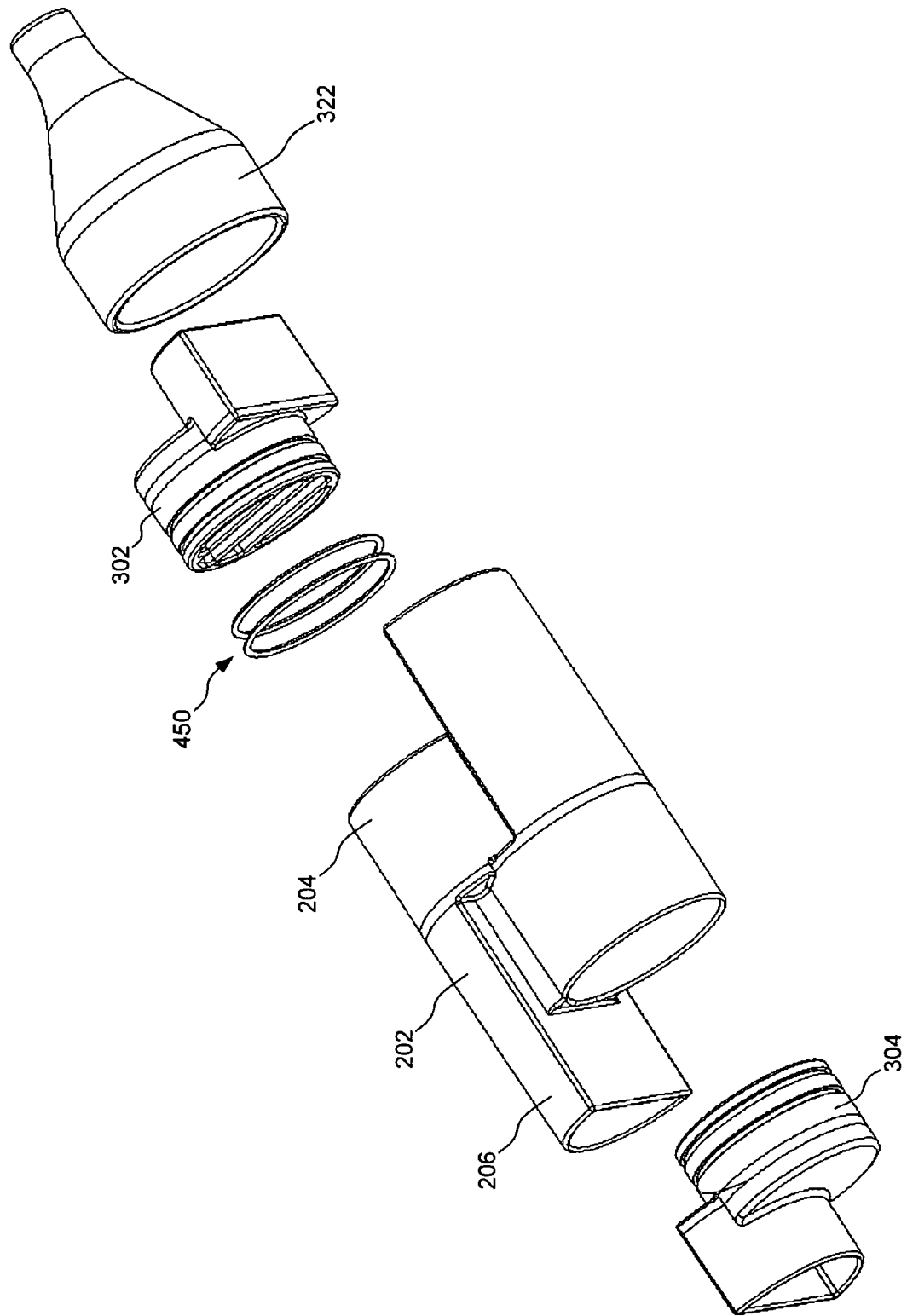
FIG. 4 is an exploded schematic diagram of a preferred embodiment of a sampling device.

FIGS. 2 to 4 show a preferred embodiment of sampling device 104. Preferably, sampling device 104 includes a central housing 202 that includes an upstream portion 204 and a downstream portion 206. Preferably, both upstream portion 204 and downstream portion 206 include provisions to receive a filter holder. In the embodiment shown in FIGS. 2 to 4, upstream portion 204 receives first filter holder 302 and downstream portion 206 includes provisions to receive second filter holder 304.

Preferably, central portion 202 is designed so that both the upstream portion 204 and the downstream portion 206 are capable of receiving substantially similar filter holders. Central housing 202 includes a first lateral side 208 and a second lateral side 210. The distance from first lateral side 208 to second lateral side 210 defines a major diameter of central housing 202 and the perpendicular distance across central housing 202 defines a minor diameter. Second lateral side 210 includes a generally flat disk-shaped end portion 212 that presents a flat end surface. First lateral side 208 is preferably includes a first air flow passage 214. First lateral side 208 preferably extends axially further outward than second lateral side 210. In other words, axial end 216 of first lateral side 208 is disposed axially further away from the center of central portion 202 than the axial end portion 212 of second lateral side 208.

Preferably, first filter holder 302 is configured to mate with upstream portion 204. In a preferred embodiment, first filter holder 302 includes a disk portion 306 and a flow passage portion 308. Disk portion 306 is designed to hold one or more filters. Preferably, disk portion 306 is designed to hold a filter conforming to an industry standard size and shape. Some common filter sizes include 25 mm and 47 mm. In an exemplary embodiment, disk portion 306 is designed to receive an industry standard 47 mm round filter. However, sampling device 106 can be sized or modified to function with or accommodate any desired filter size or type.

Given the preferred arrangement of first filter holder 302 and upstream portion 204, the two parts preferably mate in the following way. Disk portion 306 of first filter holder 302 confronts second lateral side 210 so that axial end portion 212 of second lateral side 210 faces inner axial end 310 of first filter holder 302. Outer axial end 312 of first filter holder 302 is stepped with an outer end cap 314 and flow passage portion 308 that extends axially outward from end cap 314. Specifically, flow passage portion 308 includes an outer end surface 316 that extends further outward than end cap 314.

Flow passage portion 308 is preferably designed to mate with first air flow passage 214 of first lateral side 208 of central housing 202. Preferably, axial end 216 of first air flow passage 214 and outer end surface 316 of flow passage 308 provide a regularly shaped and convenient mounting surface. In an exemplary embodiment, axial end 216 and outer end surface 316 are each semi-circular and together form a generally circularly shaped inlet port 320.

Referring to FIGS. 1 to 4, inlet port 320 serves as the upstream end of sampling device 104 and an inlet device 102 can associate with sampling device 104 at inlet port 320. In a preferred embodiment, inlet device 102 includes a downstream portion 322. Downstream portion 322 can include provisions to mate with inlet port 320. In a preferred embodiment, downstream portion 322 includes a cylindrical sleeve designed to mate with the generally circularly shaped inlet port 320.

Sampled matter is drawn from inlet device 102 and past its downstream portion 322. From here, the sampled matter enters inlet port 320. Preferably, the flow of sampled matter is divided. In a preferred embodiment, a first stream 324 of sampled matter enters flow passage portion 308 of first filter housing 302 and a second stream 326 of sampled matter enters first air flow passage 214 of central housing 202. Preferably, one or more apertures 330 are provided in first filter housing 302 to place the interior of disk portion 306 in flow communication with flow passage portion 308. The first stream 324 is then drawn through one or more first filters 328 contained within first filter housing 302. First filter 328 interacts with first stream 324 and collects a first sample.

After passing through first filter 328, first stream 324 exits the inner axial end 310 of first filter holder 302. Preferably, disk portion 306 includes holes, slots or a porous surface that allows first stream 324 to exit first filter holder 302. Preferably, first axial end portion 212, which confronts inner axial end 310, includes corresponding holes, slots or porous surface. This allows first flow 324 to enter second flow passage 264 of central housing 202. Eventually, first stream 324 exits central housing 202 at a second axial end 266.

Meanwhile, second flow 326 proceeds through first air flow passage 214, axially past first filter 328, and eventually encounters second axial end portion 262. Second axial end portion 262 preferably includes holes, slots or a porous portion similar to first axial end portion 212. Second flow 326 passes through second axial end portion 262 and enters second filter holder 304 via corresponding holes, slots or a porous portion disposed on inner axial end 410 of second filter holder 304.

Preferably, second filter holder 304 is substantially similar to first filter holder 302 except for their orientation. First filter holder 302 is disposed so that flow passage portion 308 is upstream of disk portion 306. Second filter holder 304 is oriented differently than first filter holder 302. In a preferred embodiment, second filter holder 304 is disposed generally upside down with respect to first filter holder 302. This orientation also affects the direction of flow through second filter holder 304. In second filter holder 304, the disk portion 404 is upstream of the flow passage portion 408. In other respects, the two filter holders are substantially similar and include similar structural elements.

Continuing with the description of flow, second flow 326 enters the interior portion of second filter holder 304 and interacts with second filter 428. Second filter 428 interacts with second stream 326 and collects a second sample. Second flow 326 then enters second flow passage 408 of second filter holder 304 and exits second outer surface 416 of second flow passage 408 of second filter holder 304.

Similar to the design of inlet 320, outlet 420 is comprised of axial end 266 of first air flow passage 264 and outer end surface 416 of flow passage 408, and outlet 420 is preferably designed to provide a regularly shaped and convenient mounting surface. In an exemplary embodiment, axial end 266 and outer end surface 416 are both semi-circular and together form a generally circularly shaped outlet port 420.

Referring to FIGS. 1 to 4, outlet port 420 serves as the downstream end of sampling device 104 and an air pump 106 can associate with sampling device 104 at outlet port 420. In a preferred embodiment, air pump 106 includes an upstream portion that mates with outlet port 420.

Using the features described above, it is possible to subject two filters 328 and 428 to substantially similar streams of sampled matter. In some cases, the filter material is similar. In these embodiments, it is possible to test one filter immediately and store the second filter for archival purposes. It is also possible to test each similar filter for different materials or to subject each similar filter to different kinds of tests. In some cases, it is possible to use sampling device 104 to conduct different kinds of tests for different purposes or to test for different materials. In these instances, the first filter material may be different than the second filter material.

Sampling device 104 is preferably constructed to facilitate easy and rapid assembly and disassembly. First filter holder 302 is preferably press fit onto upstream portion 204 of central housing 202 and second filter holder 304 is similarly press fit onto downstream portion 206 of central housing 202. In some embodiments, O-rings can be provided between central housing 202 and one or both of the filter holders 302 and 304. The O-rings can help to seal leakage and provide a snug fit. One or more O-rings can be used for each filter holder. In a preferred embodiment, a pair of axially spaced O-rings 450 is used with each filter holder. Preferably, a groove is provided on the respective filter holder for each O-ring. The O-rings are preferably disposed on disk portion 306 and 406 of respective first and second filter holders.

The design of sampling device 104 facilitates portable operation. Unlike other sampling devices, which are generally permanently installed fixtures, sampling device 104 can be made portable. In some embodiments, sampling device 104 can be configured to operate with sorbent tubes, which are typically 4 inches long and 0.5 inches wide. In this embodiment, sampling device 104 could have an overall length of about 8 inches and major diameter of 1.5" and minor diameter of 0.75 inches. In some embodiments, a plug filter, which has the approximate dimensions of an earplug, could be used as first filter 328 and second filter 428. In these embodiments, the overall length of sampling device 104 would be about 6 inches. It is also possible to use larger filters or create a larger sampling device 104. In some embodiments, it is possible to provide a sampling device 104 that is about 2 feet long with a 10 inch major diameter and 6 inch minor diameter. Larger sampling devices are possible, but sampling devices larger than 2 feet long may be difficult to operate as a handheld device.

Referring to FIGS. 1 and 5–8, after the filter holders have been associated with central housing 202, air pump 106 and various inlet devices 102 can be associated with sampling device 104. These inlet devices 102 can be particularly useful in embodiments where sampling device 104 is sized for portable or handheld operation. FIGS. 5–8 show different embodiments of optional inlet devices 102.

Figure 6:
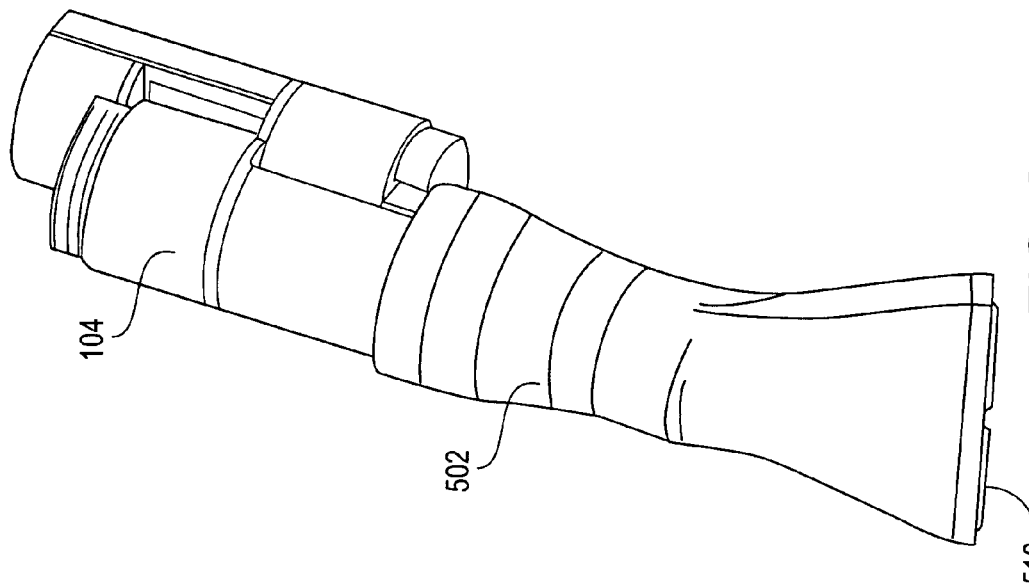
FIG. 6 is an isometric view of a preferred embodiment of a sampling device and a scraper attachment.
Figure 5:
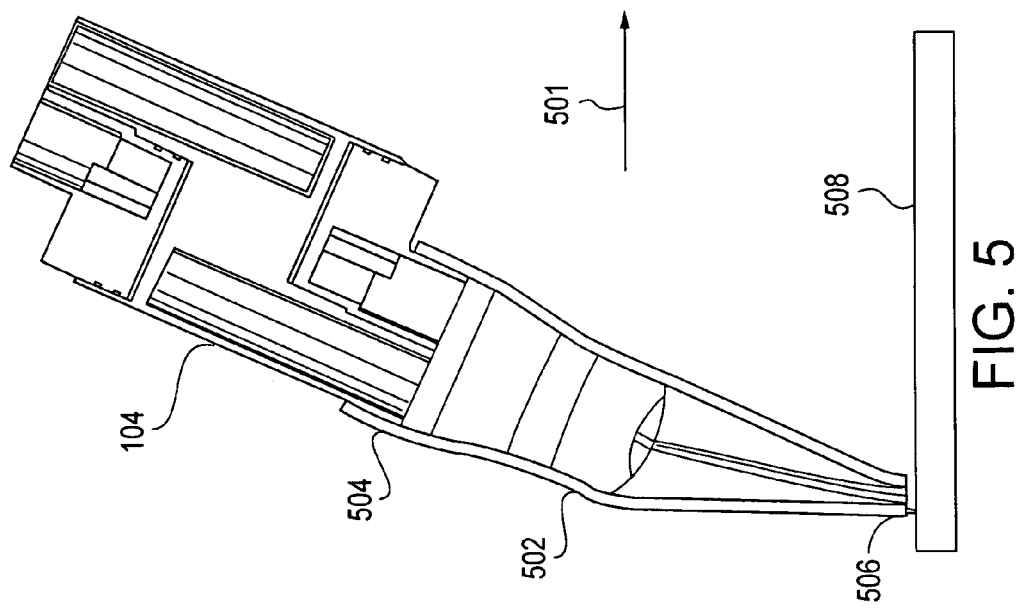
FIG. 5 is a cross-sectional view of a preferred embodiment of a sampling device and a scraper attachment.

FIGS. 5 and 6 show a preferred embodiment of a scrapper attachment 502. Scrapper attachment 502 includes a downstream end 504 that is designed to mate with sampling device 104. Scrapper attachment 502 also includes an upstream end 506 that is designed to scrap a surface 508. To assist in scraping surface 508, upstream end 506 can include one or more scraping blades 510. In the embodiment shown in FIGS. 5 and 6, scrapper attachment 502 includes two laterally spaced scrapping blades 510.

The scrapper attachment 502 and sampling device 104 assembly is preferably pulled in direction 501. The scraping blades 510 contact and disturb surface 508 and cause particulates to be released from surface 508. This helps to entrain those particles in the fluid stream caused by the suction power of air pump 106 (see FIG. 1). Those particles flow through scraper attachment 502 and into sampling device 104 where they are captured by one or more filters, as disclosed above. In a preferred embodiment, scraper attachment 502 is constructed of a static dissipative material to prevent the accumulation of particulate sampled matter on the internal surfaces of scraper attachment 502. This static dissipative material can be metallic, non-metallic and/or a metal coated material.

FIGS. 7 and 8 show other embodiments of inlet device 102. FIG. 6 shows an inlet device that is in the form of a curved wand 702. Curved wand 702 includes an outlet portion 704 that mates with the downstream portion 322 and an inlet portion 706. Curved want 702 preferably includes a U-shaped curve, and can be used to place inlet portion 706 inside wells, holes, over walls, underneath decking or any other hard to reach area.

FIG. 8 shows an embodiment of inlet device 102 that takes the form of a straight wand 802. Straight wand 802 includes an inlet 806 and an outlet 804. Straight wand 802 can be used to extend the reach of a user and place inlet 806 near distant objects or test subjects. Straight wand 802 can also be used to sample the interior of a generally inaccessible closed volume that cannot be opened, for example, a shipping container, box or package.

Preferably, sampling device 104 is constructed of a static dissipative plastic material. Other associated devices, for example, inlet devices and tubing or connectors used to attach air pump to sampling device 104 can also be made of a static dissipative plastic material to prevent the accumulation of particulate sampled matter on the internal surfaces of sampling device 104 or other associated devices. This static dissipative material can be metallic, non-metallic and/or a metal coated material.

Each of the various components, steps or features disclosed can be used alone or with other components, steps or features. Each of the components, steps or features can be considered discrete and independent building blocks. In some cases, combinations of the components, steps or features can be considered a discrete unit.

While various embodiments of the invention have been described, it will be apparent to those of ordinary skill in the art that may more embodiments and implementations are possible that are within the scope of the invention. Accordingly, the invention is not to be restricted except in light of the attached claims and their equivalents.

What is claimed is:

1. A sampling device configured to cooperate with an inlet device at an inlet and an air pump comprising:
   a central housing including an upstream portion and a downstream portion;
   the upstream portion including provisions to receive a first filter holder, the first filter holder containing a first filter;
   the downstream portion including provisions to receive a second filter holder, the second filter holder containing a second filter;
   wherein sampling matter is drawn into the inlet and divided into a first stream that interacts with the first filter and a second stream that interacts with the second filter;
   wherein the first filter holder and the second filter holder are substantially similar in shape and size;
   wherein the first filter holder is disposed upstream of the second filter holder;
   wherein the second stream enters a first flow passage of the central housing after entering the inlet;
   wherein the first filter holder includes a flow passage adjacent to the first flow passage of the central housing;
   wherein the flow passage of the first filter holder and the first flow passage of the central housing form the inlet;
   wherein the flow passage of the first filter holder is generally semi-circular and the first flow passage of the central housing is generally semi-circular and both the flow passage of the first filter holder and the first flow passage of the central housing form a generally circular inlet;
   wherein the first filter holder is disposed on an upstream portion of the central housing and the second filter holder is disposed on a downstream portion of the central housing; and
   wherein the flow passage of the first filter holder and the first flow passage of the central housing form the inlet.

2. A sampling device comprising:
   a central housing including an upstream portion and a downstream portion;
   a first filter associated with the upstream portion;
   a second filter associated with the downstream portion;
   wherein sampling matter is drawn into the inlet and divided into a first stream that interacts with the first filter and a second stream that interacts with the second filter;
   wherein the second filter is axially spaced from the first filter;
   wherein the second stream enters a flow passage prior to interacting with the second filter;
   wherein first stream enters a flow passage after interacting with the first filter;
   wherein a first filter holder includes a disk portion containing the first filter and a flow passage portion;
   wherein a second filter holder holds the second filter and is substantially similar to the first filter holder; and
   further comprising a scraper attachment;
   wherein the second filter holder is laterally spaced from the first filter holder.

* * * * *